United States Patent [19]
Damon

[11] Patent Number: 5,466,151
[45] Date of Patent: Nov. 14, 1995

[54] SPRING-LOCKED ORTHODONTIC BRACKET

[75] Inventor: Dwight H. Damon, Spokane, Wash.

[73] Assignee: Damon Family Limited Partnership, Spokane, Wash.

[21] Appl. No.: 267,188

[22] Filed: Jun. 28, 1994

Related U.S. Application Data

[63] Continuation-in-part of Ser. No. 140,690, Oct. 20, 1993, Pat. No. 5,429,500, which is a continuation of Ser. No. 45,529, Apr. 8, 1993, Pat. No. 5,275,557.

[51] Int. Cl.⁶ .................................................... A61C 3/00
[52] U.S. Cl. ................................ 433/10; 433/14; 433/13
[58] Field of Search ................................ 433/10, 11, 13, 433/14

[56] References Cited

U.S. PATENT DOCUMENTS

| | | | |
|---|---|---|---|
| 2,549,528 | 4/1951 | Russell | 433/13 |
| 2,671,964 | 3/1954 | Russell et al. | |
| 3,131,474 | 5/1964 | Johnson | 433/14 |
| 3,578,744 | 5/1971 | Wildman | 433/14 |
| 4,023,274 | 5/1977 | Wallshein | 433/11 |
| 5,094,614 | 3/1992 | Wildman | 433/14 |
| 5,275,557 | 1/1994 | Damon | 433/10 |
| 5,322,435 | 6/1994 | Pletcher | 433/10 |

Primary Examiner—Cary E. O'Connor
Attorney, Agent, or Firm—Wells, St. John, Roberts, Gregory & Matkin

[57] ABSTRACT

A self-locking orthodontic bracket includes a supporting base and transversely spaced tying lugs interrupted by a transverse archwire slot. A closure mounted on the bracket includes a movable cover slidably overlapping an anterior surface across the bracket. The closure is supported by sliding guides that engage opposed side surfaces of the tying lugs. A transverse flat spring is recessed within the fixed wall to selectively engage indented areas on the posterior surface of the cover and serve as a detent. The detent selectively positions the cover in an open or closed position relative to the archwire slot. The brackets are preferably installed in two sets for attachment to the upper and lower teeth with the covers of both sets being movable to their open positions in common inferior directions. This facilitates visualization of the open archwire slot and adjacent bracket surfaces by attending professionals.

40 Claims, 11 Drawing Sheets

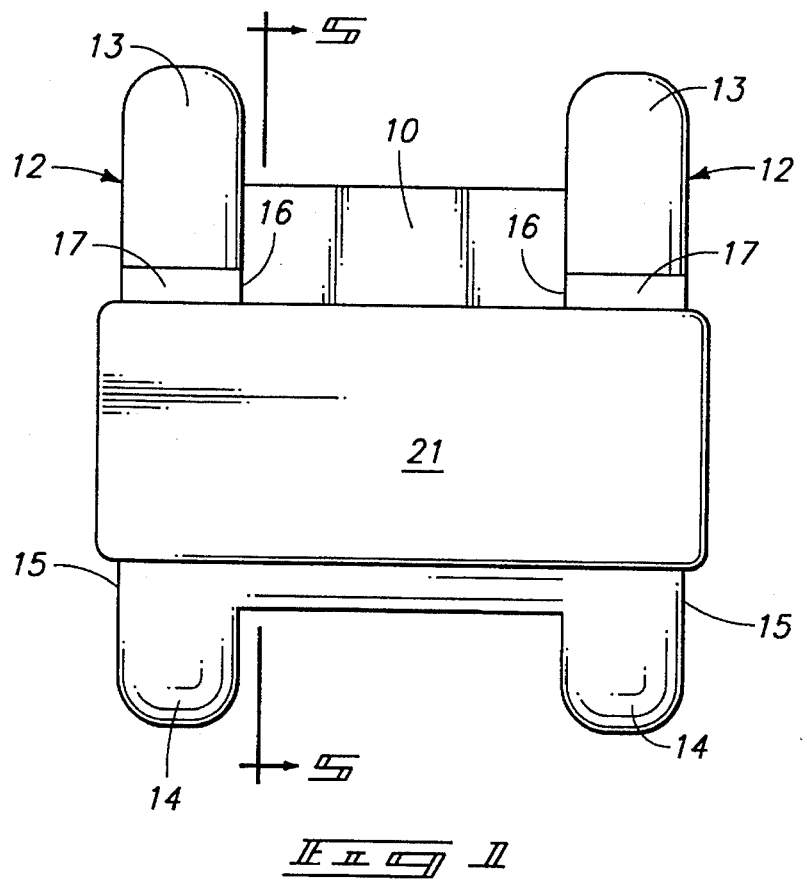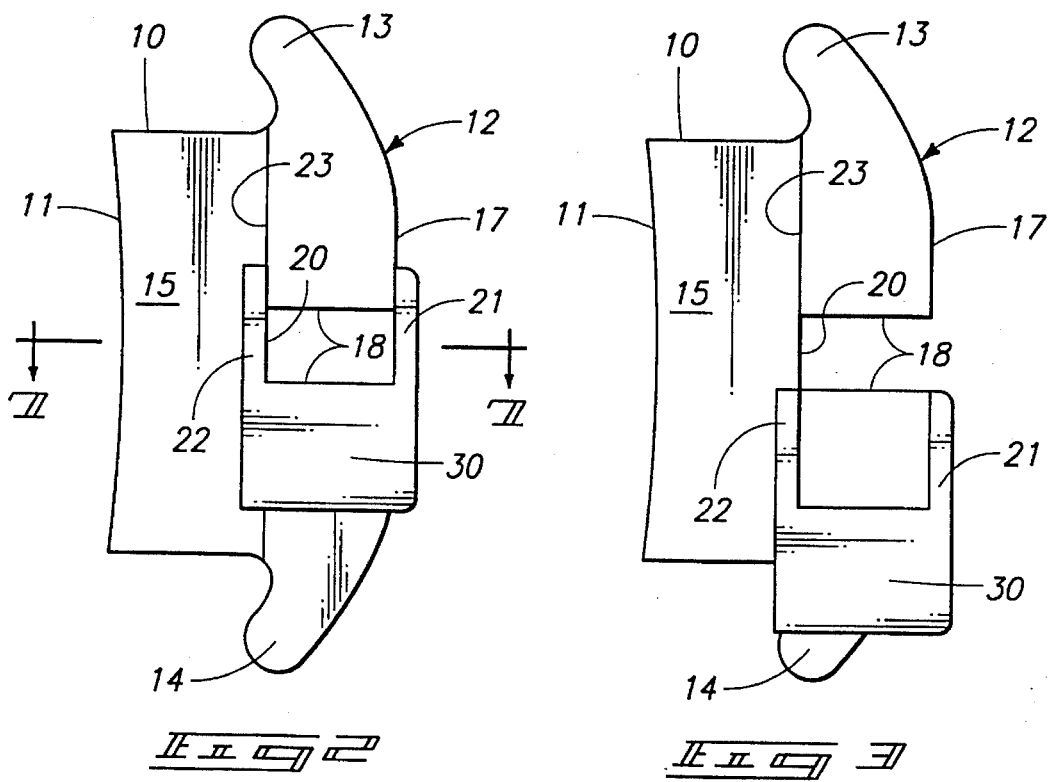

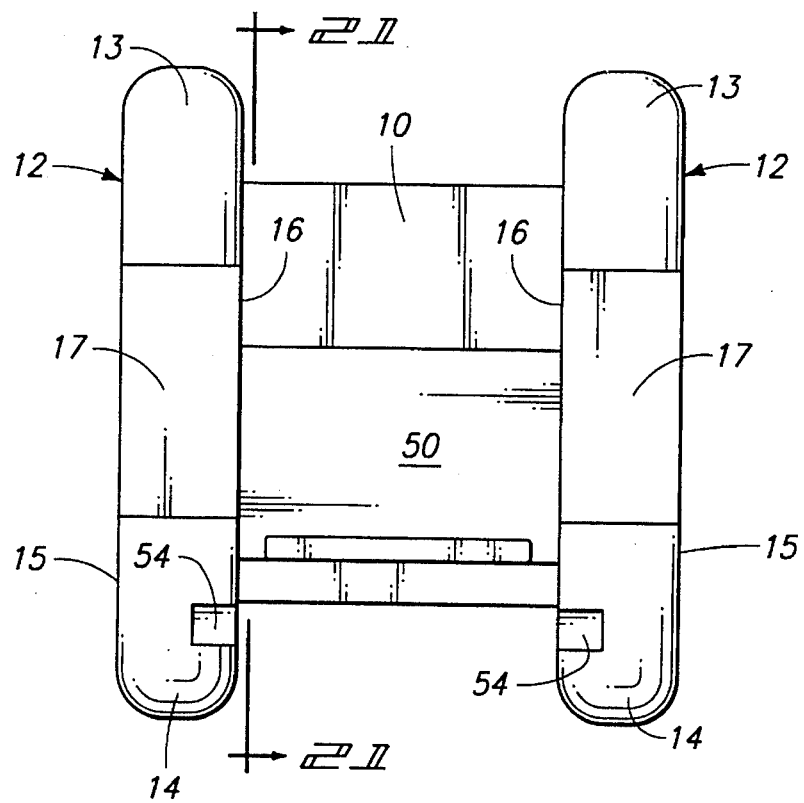
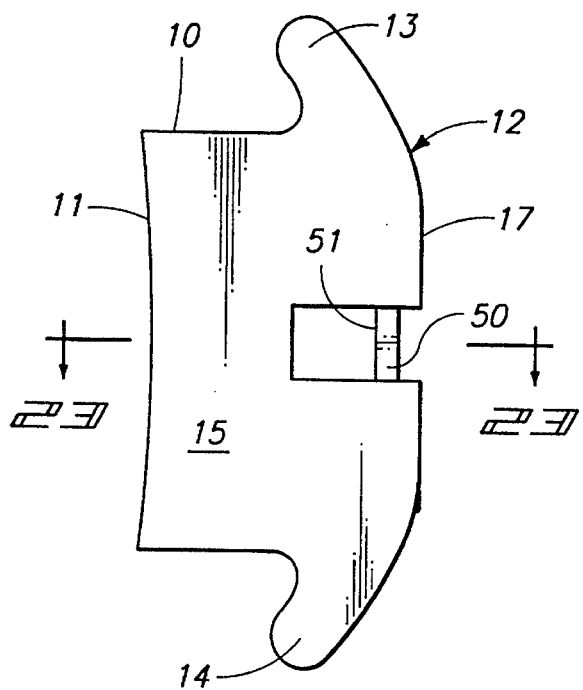

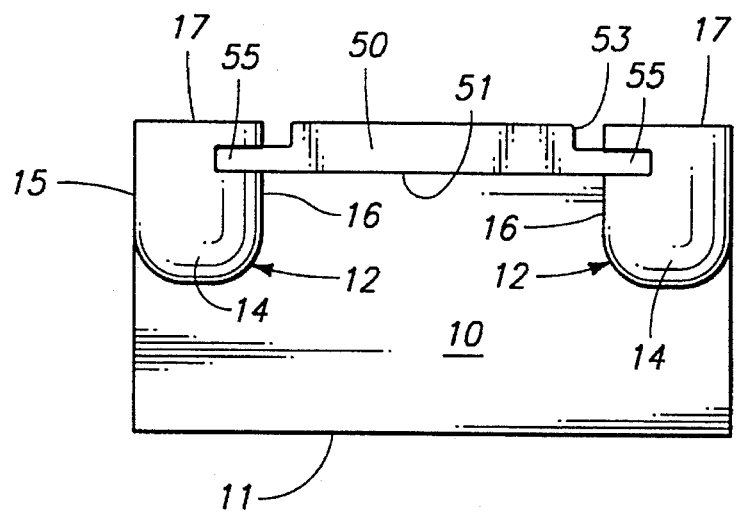
_Fig 20_
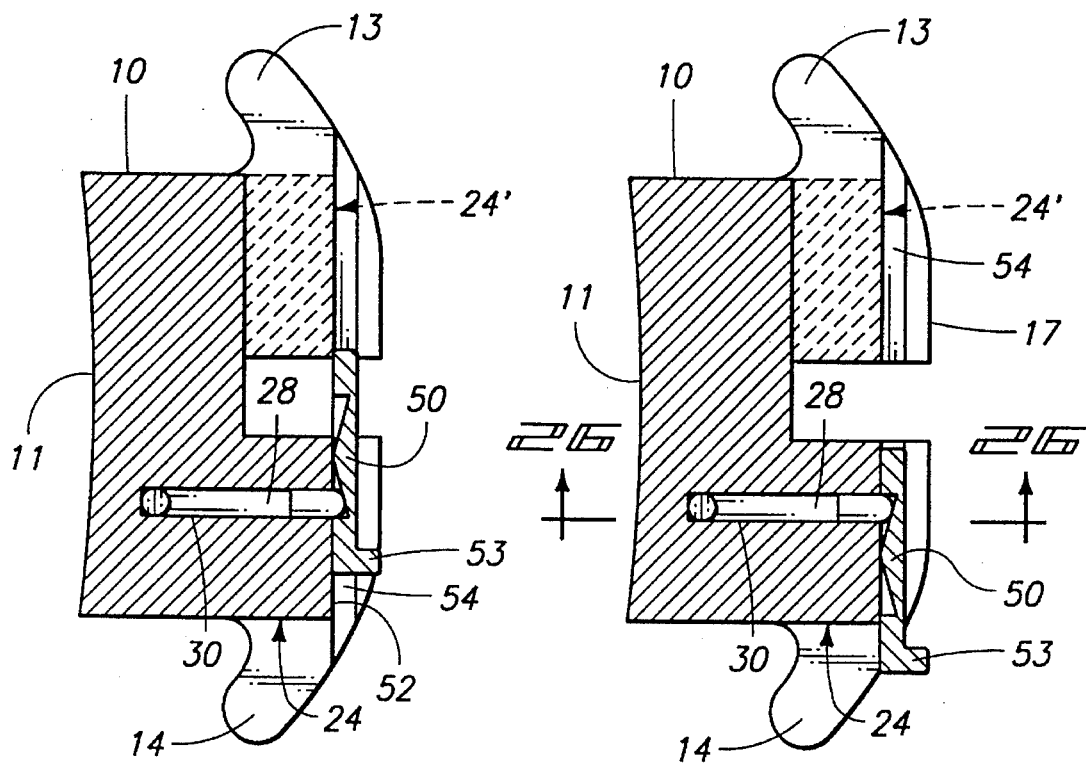
_Fig 21_  _Fig 22_

SPRING-LOCKED ORTHODONTIC BRACKET

RELATED APPLICATION

This is a Continuation-in-part of patent application Ser. No. 140,690, filed on Oct. 20, 1993, which is titled "Self-Locking Orthodontic Bracket", now U.S. Pat. No. 5,429,500, which in turn is a Continuation-in-part of patent application Ser. No. 045,529, filed on Apr. 8, 1993, and now U.S. Pat. No. 5,275,557, issued on Jan. 4, 1994, also titled "Self-Locking Orthodontic Bracket".

TECHNICAL FIELD

This disclosure pertains to self-locking or ligatureless orthodontic brackets.

BACKGROUND OF THE INVENTION

Orthodontic brackets attached to teeth are adapted to engage an archwire that exerts forces upon them to move the teeth. Such brackets typically include an archwire slot for reception of the archwire. An archwire slot can have any desired cross-sectional configuration or size to match requirements of the archwire, or archwires, that are to be engaged within the slot.

Orthodontic brackets are typically bonded to a tooth or to a tooth band with the archwire slot oriented parallel to the occlusal plane. However, the slot can also be angularly oriented across the bracket when desired.

Most brackets in use today include extensions that project upwardly and downwardly at the top and bottom of the installed bracket, respectively. These extensions permit the archwire to be held within the archwire slot of the bracket by means of a twisted wire (ligature) or an elastomer O-ring.

Numerous attempts have been made to design brackets that are self-locking or ligatureless. A detailed discussion of patents and publications describing various closures that have been proposed for the archwire slots of such orthodontic brackets can be found in Wildman U.S. Pat. No. 5,094,614, issued Mar. 10, 1992, which is hereby incorporated into this disclosure by reference.

As recognized in the Wildman patent, an ideal locking device for an orthodontic bracket should leave the top and bottom of the bracket, including the projections conventionally used for anchoring the tying wires, free to receive other attachments or auxiliary devices.

The Wildman patent discloses a slidable closure that engages the front of the archwire. The closure is recessed from the front or anterior surfaces of the disclosed bracket. This is also true of sliding closures shown in Russell et al. U.S. Pat. No. 2,671,964, which was issued on Mar. 16, 1954 and in Johnson U.S. Pat. No. 3,131,474, which was issued on May 5, 1964. The fact that such recessed sliding closures require the archwire also to be recessed within the archwire slot before the closure can be moved over the archwire makes it very difficult for the user to visually confirm that the archwire is properly seated within the archwire slot to facilitate closing of the slidable cover.

When using a conventional bracket and tying wires, proper seating of the archwire can be confirmed by visually noting that the anterior surface of the archwire is flush with the anterior surface of the bracket. It is desirable that a self-locking bracket provide similar visual reference capabilities to the user. This cannot be attained where no anterior surface of the bracket is available for visually referencing the position of an archwire within the archwire slot of the bracket.

A flush-mounted closure in the form of a spring clip is shown in various embodiments illustrated within Wallshein U.S. Pat. No. 4,023,274, issued on May 17, 1977. In FIGS. 4A and 4B of the Wallshein patent, there is illustrated a spring clip having a closure panel that extends across the full width of a bracket and covers aligned slots in two separate lugs. However, the spring clip also covers the bottom of the bracket and presents a separable bracket element that must be attached to the bracket prior to its utilization. A sliding closure is more easily manipulated than a spring clip. Slidable closures are particularly desirable because they substantially reduce the time required for opening and closing of the archwire slots during periodic adjustment of the archwire and brackets.

The present bracket was designed to mount an archwire flush with an anterior surface of an orthodontic bracket to facilitate visual positioning of the archwire during orthodontic treatment. It also was designed to utilize a sliding closure that can be permanently retained on the bracket during use, whether the closure is left in an open or closed condition. This guards against accidental release of the closure while the bracket is worn on a tooth.

Most importantly, the closure has been designed to leave the usual tying extensions that protrude from the top and bottom of the bracket fully accessible to other orthodontic attachments for the application of torsional forces to the teeth. The exposed tying lugs remain always available for repositioning of the bracket and tooth by use of tying wires or other conventional attachment systems.

The present bracket also includes a closure that can complete a continuous tube surrounding the archwire when the closure is in a closed position. This can be effectively achieved in a Siamese bracket configuration without covering or interfering with projecting extensions on the bracket.

BRIEF DESCRIPTION OF THE DRAWINGS

Preferred embodiments of the invention are described below with reference to the accompanying drawings, which are briefly described below.

FIG. 1 is an elevational view of an assembled bracket with the cover in a closed position;

FIG. 2 is a side view of the bracket;

FIG. 3 is a side view of the bracket with the cover in an open position;

FIG. 18 is an elevational view of a second embodiment of the bracket;

FIG. 19 is a side view of the bracket shown in FIG. 18;

FIG. 20 is a bottom view of the bracket;

FIG. 21 is a sectional view taken along line 21—21 in FIG. 18, an intermediate fixed wall being shown in phantom;

FIG. 22 is a sectional view similar to FIG. 21, showing the closure in an open position;

DETAILED DESCRIPTION OF THE PREFERRED EMBODIMENTS

Figure 4:
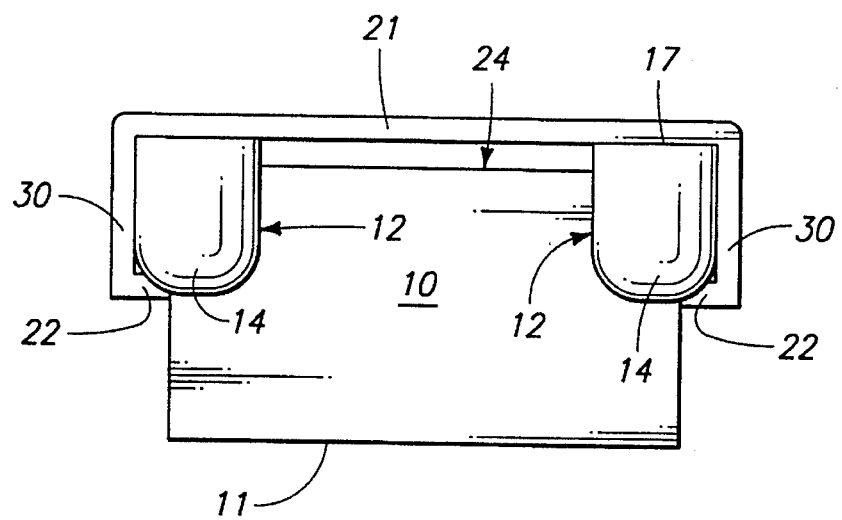
FIG. 4 is a bottom view of the bracket.

This disclosure of the invention is submitted in furtherance of the constitutional purposes of the U.S. Pat. Laws "to promote the progress of science and useful arts" (Article 1, Section 8).

Two illustrative forms of the self-locking orthodontic bracket are illustrated in the drawings. A first preferred embodiment is shown in FIGS. 1–12. An alternative embodiment is shown in FIGS. 18–26.

When referring to the illustrated forms of the bracket, the front surfaces of each bracket, directed outwardly from a supporting tooth, shall be referred to as anterior surfaces. Conversely, the rear surfaces, which face toward the tooth, shall be termed posterior surfaces. Directions along the bracket generally parallel to the incisal or occlusal line shall be referred to as having width and being transverse. Conversely, perpendicular directions extending between the gingival line and the incisal or occlusal line shall be referred to as the height of the bracket. The upright surfaces across the bracket shall be termed its side surfaces and the surfaces along the top and bottom of the bracket shall be termed the incisal or occlusal surface or the gingival surfaces.

When referring to the directions of movement of the cover relative to the bracket, the terms "inferior" and "superior" shall be sued in an anatomical sense oriented in relation to a patient wearing the bracket. Thus, if the cover is moved inferiorly, it will be moved in a downward direction. Conversely, if the cover is moved superiorly, it will be moved in an upward direction.

The incisal and occlusal surfaces, or the gingival surfaces, of the bracket are normally interrupted by projections that form cleats or anchors for tying wires and other attachment devices. However, the basic features of the present improvement can be applied to bracket structures having no such extensions. The configurations of these extensions, when present, can take any desired conventional or unconventional form. The extensions at the top and bottom of the bracket can be located in different planes. The extensions at the top of the bracket can be located in a plane different from that of the extensions at the bottom of the bracket. The extensions might also have the same or a different configuration at the top of the bracket than at the bottom of the bracket.

The archwire slots shown in FIGS. 1–17 of the illustrative drawings are aligned transversely across each bracket in a direction parallel to the incisal or occlusal surface for general illustration purposes. However, the archwire slot across each bracket can be oriented at any desired angular configuration relative to its incisal or occlusal surfaces to effect a desired degree of tipping to a supporting tooth. In addition, the bracket can be oriented angularly relative to the supporting base, thereby providing angular forces to the slot and engaged archwire when secured to a supporting tooth.

In order to properly fit upon the exterior surface of a selected tooth, the posterior base surface across each bracket must be molded or otherwise formed to conform to the tooth with the archwire slot at the desired angular relationship to the archwire upon installation. Various placement angles can be provided on selected brackets by rotating the anterior surface contour across the bases of the brackets within a set. Alternatively, the archwire slots in a set of brackets can be arranged at selected angles by rotating the position of the protruding elements of each bracket relative to a common base structure having a properly contoured posterior base surface. The archwire slot is then formed on the protruding portion of the bracket to match the amount of tipping to be imparted to a given tooth.

While the illustrated archwire slot is shown oriented perpendicular to the anterior surfaces of the bracket, it can be formed at any desired angle to the anterior surfaces, depending upon the desired torquing to which the supporting tooth is to be subjected.

The illustrated brackets can be bonded directly to a tooth or can be mounted on a tooth band for attachment to a tooth at either the facial or lingual tooth surfaces.

The present bracket can be made from any suitable material, including metals, plastics and ceramics, as well as a combination of such materials. The bracket and closure have generally been designed to be fabricated of metal, but the choice of materials is not critical to understanding or using this invention. The only limitation with regard to materials is the ability to efficiently fabricate or mold the bracket and closure as a cooperative mechanism to engage an archwire during orthodontic procedures.

The general concepts of the invention can best be understood from a study of the first embodiment of the assembled orthodontic bracket, illustrated in FIGS. 1–12. This form of the bracket includes a movable closure separately shown in FIGS. 8–11.

The illustrated bracket includes a supportive base 10 having a posterior surface 11 adapted to be bonded to a tooth or tooth band. It is shown as a "Siamese" bracket, having two transversely spaced lugs or projections across the base 10. A single lug bracket, with or without protruding extensions, can alternately be used.

A pair of lugs 12 project anteriorly from base 10. While not limited to such applications, the lugs are shown as tying lugs. Each lug 12 includes opposed extensions 13 and 14 that project outwardly between transversely spaced side surfaces formed on the bracket. At a minimum, the tying lugs 12 each include an outer side surface 15. In addition, the tying lug configurations shown in the drawings further include inwardly facing side surfaces 16 formed across each tying lug 12.

The bracket also includes an anterior surface 17 across the front of each tying lug 12. The anterior surface 17 is illustrated as being planar, but can be curved if desired. It is interrupted by the opening of a transverse archwire slot formed distally from the anterior surface 17. The archwire slot spans the full width of the bracket, where it opens across the bracket side surfaces 15 (see FIGS. 2, 3 and 7).

The archwire slot includes side slot surfaces 18 and an anterior slot surface 20. The slot surfaces 18 and 20 are sized and configured in a manner complementary to the size and shape requirements of an archwire (or archwires) adapted to be received within the archwire slot. While the illustrated slot is rectangular and is designed specifically for reception of a complementary rectangular archwire, it is to be understood that the slot can be configured as a cylinder or other cross-sectional shape in the manner presently known with respect to orthodontic bracket design. In use, the slot is partially or completely filled by the cross-sectional configuration of one or more archwires located within it.

A closure complementary to the archwire slot is also provided on the illustrated bracket. It includes a movable cover 21 that slidably engages the anterior surface 17. Cover 21 has a width that spans the full width of the tying lugs 12 between their respective side surfaces 15. Its perpendicular width is greater than the corresponding width across the archwire slot at the anterior surface 17 of the bracket.

The closure further includes a pair of guides 22 spaced transversely apart from one another along the width of the bracket. The guides slidably engage opposed side surfaces 15 along transverse surfaces 23. The transverse surfaces 23 can be in the form of a posterior ledge extending along each side of the bracket or can be formed within a receiving groove for a guide 22. The preferred ledge configuration is illustrated in the drawings.

The transverse surfaces 23 preferably extend along the full height of the lug side surfaces on which they are formed, as can be seen in FIGS. 2 and 3. This permits the closure to be installed or removed from the bracket at either its upper or lower ends. However, one or both ends of each surface 23 might terminate along the lug side surface on which it is formed at locations short of its respective ends. Surfaces 23 can also include protrusions (not shown) which will serve as stops to limit the amount of closure motion relative to the bracket.

The sliding guides 22 are illustrated as being parallel to the portions of the anterior surface 17 slidably engaged by cover 21. Thus, the movement imparted to the supported cover 21 as it slides along the surfaces 23 will maintain it in a parallel position with its inner surface flush against the overlapped areas of anterior surface 17. This will maintain cover 21 in a closely adjacent position to the stationary bracket structure regardless of whether cover 21 is in its open or closed positions. If the anterior surface 17 is transversely curved, the guides 22 and surfaces 23 might be similarly curved to achieve the desired flush sliding relationship between surface 17 and cover 21.

Figures 5, 6:
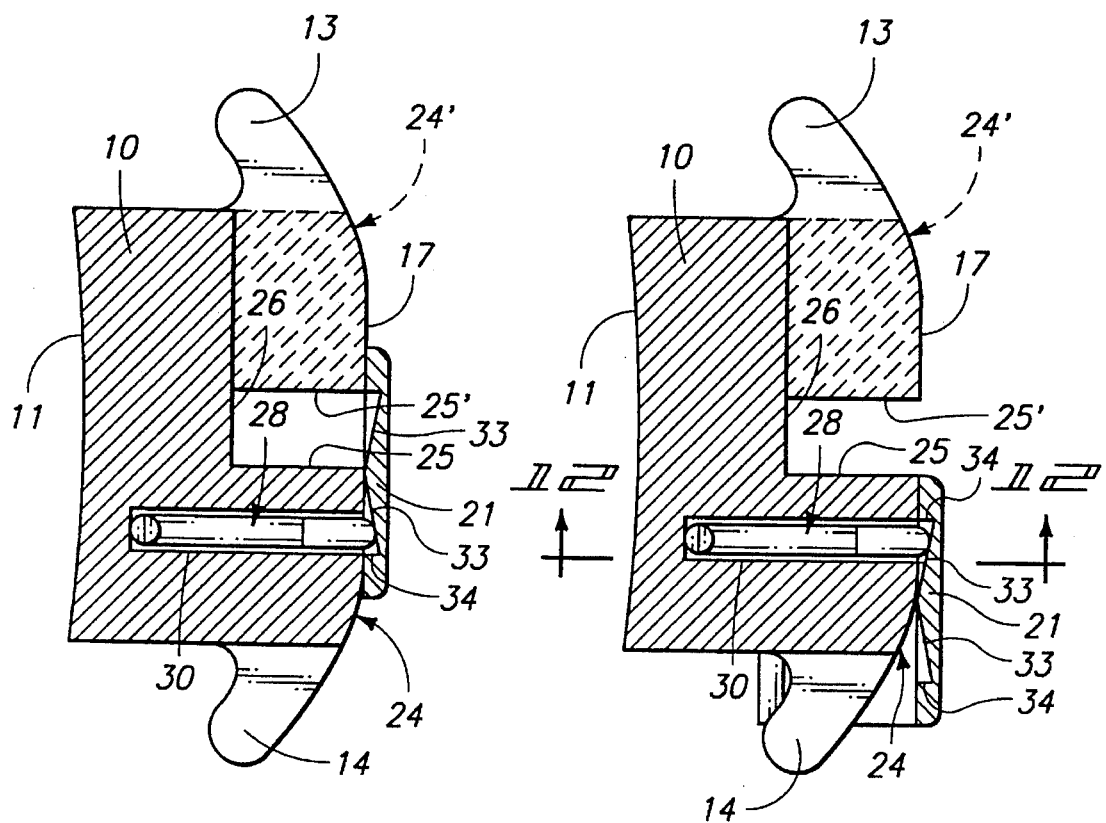
FIG. 5 is a sectional view as seen along line 5—5 in FIG. 1, an alternate intermediate fixed wall being illustrated in phantom.
FIG. 6 is a sectional view similar to FIG. 5, showing the cover in an open position.

Movement of the cover and guides relative to the tying lugs 12 alternately positions the closure in (1) a first position with the cover clear of the archwire slot (FIGS. 2, 5) or (2) a second position with the cover 21 overlapping the width and height of the archwire slot (FIGS. 3, 6).

The above description includes only those elements basic to Siamese brackets, which include transversely spaced tying lugs protruding from a supporting base. However, additional strength and the benefits of an enclosed archwire tube can be imparted to this bracket by also providing a fixed transverse wall between the inner side surfaces 16 of the respective tying lugs 12. This wall, shown at 24, should preferably structurally interconnect the tying lugs 12 and base 10, although it can be formed independently of the lugs 12 or base 10 if desired.

Wall 24 includes at least one inner surface 25 aligned with a side slot surfaces 18 in the respective tying lugs 12. Either the wall 24 or base 10 also preferably includes a perpendicular transverse surface 26 aligned with the anterior slot surfaces 20 along the respective tying lugs 12.

FIGS. 5 and 6 illustrate the option of constructing the bracket with an intermediate fixed wall 24 between the tying lugs 12 which forms only one side surface 25. In additions, it is possible to construct the bracket with a fixed wall having an inner transverse surface spaced outwardly from the archwire slot. In such a construction, the aligned slots though the spaced lugs 12 will serve as the archwire slot and the archwire will be unsupported between them.

The phantom crosshatching in FIGS. 5 and 6 illustrates a second transverse fixed wall section 24' which presents a second aligned side surface 25' between the lugs 12. This is the preferable form of the bracket, but this disclosure is not to be limited to such features. The resulting open slot along the bracket is then formed continuously from one side of it to the other, eliminating the sharp edged corners that would otherwise be presented at the inner side surfaces 16 of the tying lugs 12.

Wall 24 can be constructed as a rather narrow or wide structure having surfaces forming a continuation of one or two sides of the transverse archwire slot, or none of them. However, it is to be understood that the thickness of wall 24, which can be expanded by addition of the section 24' shown in phantom in FIGS. 5 and 6. When fully extended throughout the full height of the bracket across the illustrated base 10, the fixed wall will still leave extensions 13 and 14 protruding openly at the top and bottom of the bracket for tying purposes.

Figure 7:
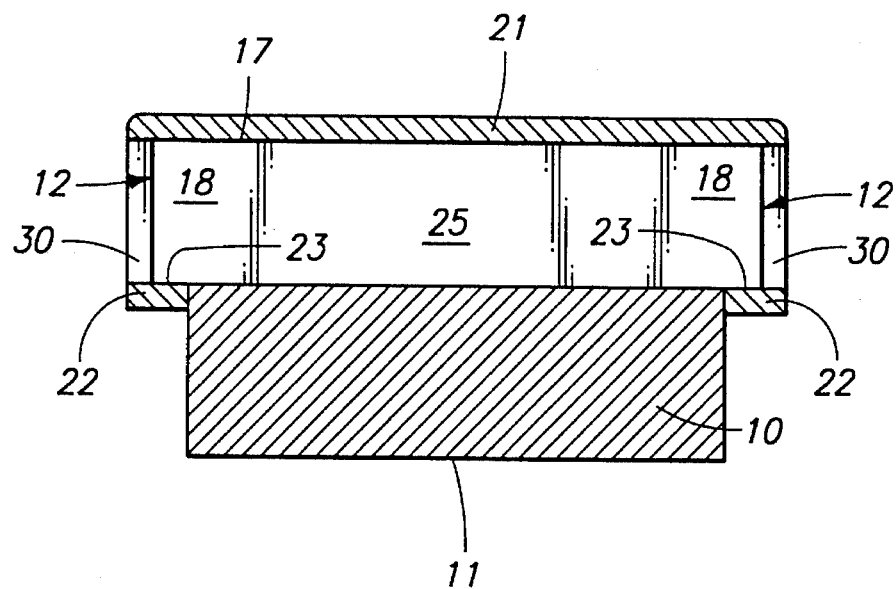
FIG. 7 is a sectional view taken along line 7—7 in FIG. 2.
Figure 8:
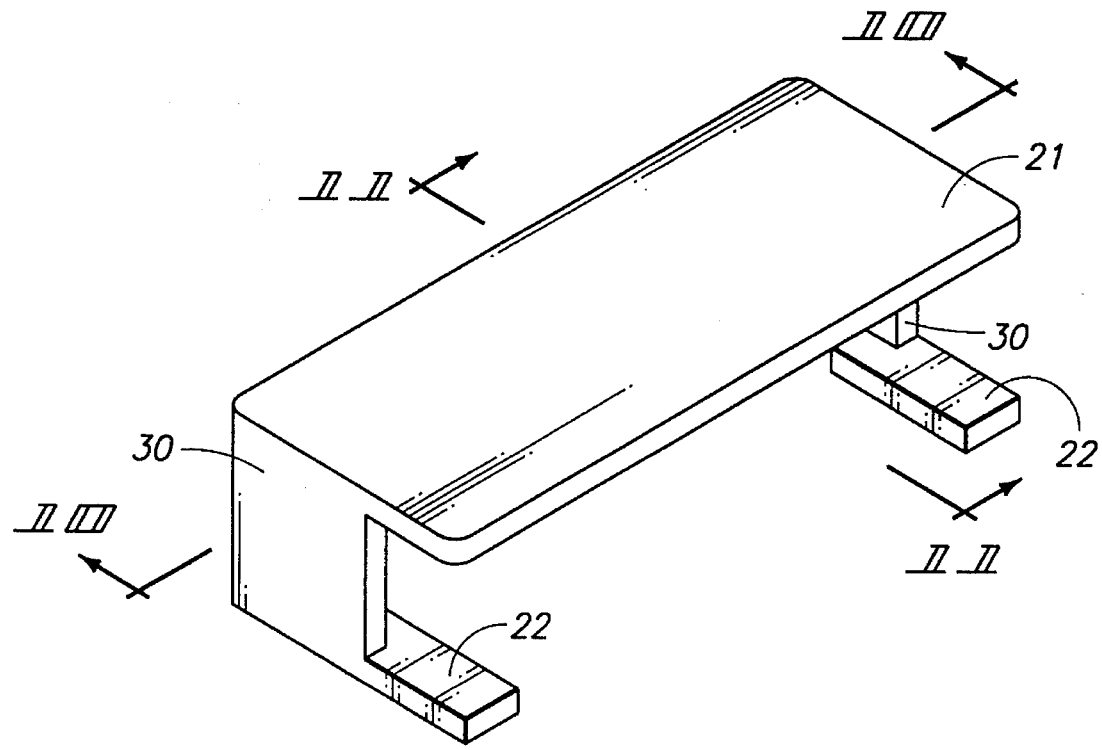
FIG. 8 is a top perspective view of the closure shown in FIGS. 1–7.
Figure 9:
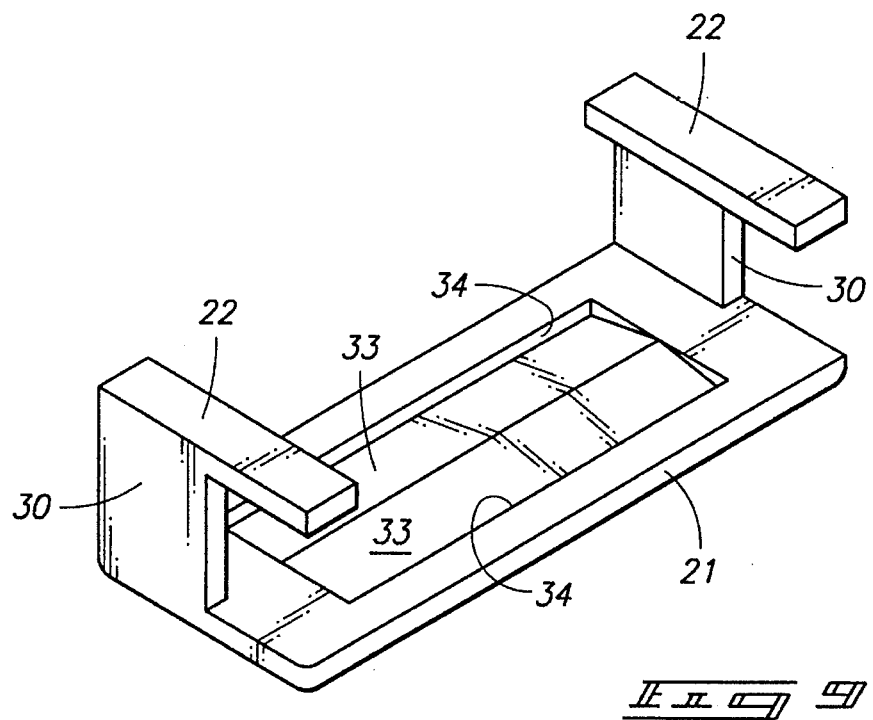
FIG. 9 is a bottom perspective view of the closure.
Figure 10:
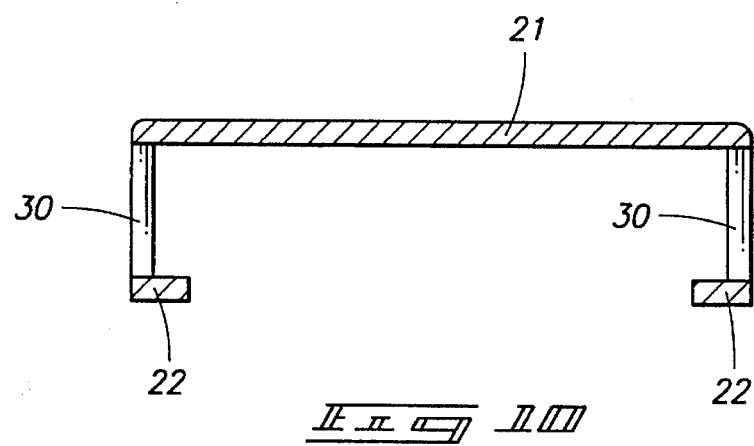
FIG. 10 is a transverse sectional view of the cover as seen along plane 10—10 in FIG. 8.
Figure 11:
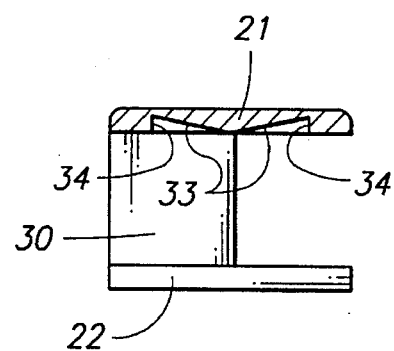
FIG. 11 is a sectional view of the cover taken along plane 11—11 in FIG. 8.

As can be seen in FIG. 7, the side slot surfaces 18 along the tying lugs 12 and each aligned inwardly facing surface 25 and 25' within transverse wall 24 merge to form continuous inner slot surfaces extending across the full width of the bracket. They intersect similarly merging anterior slot surfaces 20 and 26, as previously described. When enclosed by cover 21, as shown in FIGS. 2 and 5, these surfaces and the movable cover preferably form a fully enclosed tube for engagement of an archwire across the complete width of the bracket.

Cover 21 and guides 22 are structurally interconnected by an interposed pair of rigid support members shown at 30. The support members 30, together with cover 21 and guides 22 form a separable closure generally illustrated in FIG. 8. This closure can be molded or fabricated independently from the bracket. It should be assembled on the bracket prior to installation of the bracket on a tooth or tooth band. While the closure is normally retained on the bracket during its use, it can be forced free from the bracket for replacement purposes or when use of the closure is not required. The design of the bracket and closure should be such that removal of the closure can only be achieved by substantial prying movement, such as might be applied through use of a scaler or by applying a substantial spreading force by manual pliers to the support members 30, thereby releasing guides 22 from engagement with the transverse surfaces 23 along the side surfaces of lugs 12.

Guides 22 are located on the bracket in positions that are posterior to the open slot formed transversely through it, As can be seen in FIGS. 2 and 3, the support members 30 are offset from the center line of the closure to assure that there is adequate clearance across the full width of the archwire slot when the cover 21 is in its closed position. Thus, transverse sliding movement of the guides 22 and support members 30 does not block or restrict access to any portion of the open transverse archwire slot.

The support members 30 are respectively located adjacent to the side surfaces 15 across the tying lugs 12. Each support member 30 leads posteriorly from the cover 21 to one of the guides 22.

When in its open position, as shown in FIGS. 3 and 6, cover 21 will leave the slot clear for movement of an archwire into or out from the slot. In addition, the protruding extensions 13 at all times remain clear and accessible for tying or attachment purposes.

It is also desirable that cover 21 not be accidentally released from engagement with the supporting bracket structure while within the mouth of a patient. This can be achieved by provision of positive stops (not shown) on the guides 22 or transverse surfaces 23 to limit the extent of sliding movement of cover 21 along the bracket's side surfaces 15. Removal of cover 21 might also be prevented by protrusions (not shown) that extend outwardly from side surfaces 15 in the path of the rigid support members 30 that interconnect cover 21 and guides 22. In the embodiment illustrated, outward movement of cover 21 is limited by the interengaging action of a detent (see FIGS. 5, 6 and 12). The design and operation of acceptable detents, locks and motion limiting features is subject to many variations.

It is preferable that cover 21 be releasably locked in its closed position to ensure against accidental release of an archwire received within the archwire slot. Releasable detents or locks can be provided between the cover 21 and the bracket or between the guides 22 and the bracket. The preferred form of detent includes a recessed flat spring 28 within the fixed wall 24 and a complementary indentation across the posterior surface of cover 21 (see FIG. 9).

Spring 28 is located in the supporting wall 24 within a surrounding transverse recess 30. Recess 30 is open to the anterior surface 17 of the bracket across the fixed wall 24. It can also be extended into the lug structures at each side of the fixed wall if desired. The inwardly open recess 30 extends distally to a recess base 31 between opposed recess end walls 32.

Spring 28 is a resilient flat spring bent formed from a length of wire, which can have various cross-sectional shapes, such as circular, oval, square and rectangular. It can be either straight or bent. In the illustrated spring examples, each spring includes a bent section that normally extends beyond the anterior surface 17 across the bracket. Spring 28 can be produced with any bent or flat shape having a normal configuration that partially extends beyond the anterior surface 17 across the fixed wall 24 of the bracket. In this manner, the cover 21 can be releasably maintained in one of its first or second positions by engagement of the spring 28 within a complementary indentation presented at the posterior surface of cover 21. Spring 28 can be constructed of any suitable metallic or non-metallic material capable of deformation between a normal extended condition and a compressed condition as the cover 21 moves over it.

The flat spring 28 is movably supported within recess 30. It can be compressed between cover 21 and the boundaries of recess 30. If a cantilevered spring action is desired, one section of the spring can be actually be fixed or secured within the recess 30. Recess 30 can be relatively deep, as shown, or can be relatively shallow to support flatter spring configurations.

It is preferable that the recess 30 and flat spring 28 be oriented transversely across the bracket. This permits the spring 28 to present a defined resistance to cover movement in a direction perpendicular to the length of the flat spring. However, the flat spring could alternately be oriented parallel to the directions of cover movement if desired.

The posterior surface of cover 21 includes at least one indentation sized and positioned to receive the bent section of spring 28. Cover 21 is releasably maintained in one of its positions by engagement of the protruding bent section of spring 28 within the indentation.

The illustrated indentation extends substantially across the width of the cover 21. The indentation includes oppositely inclined areas 33 which terminate along abrupt walls 34 that serve as motion limits in response to engagement of spring 28. The positioning of abrupt walls 34 defines the closed and open positions of cover 21, respectively, as illustrated in FIGS. 5 and 6. The progressive spring forces exerted on the posterior surface of cover 21 along inclined areas 33 assist in providing tactile "feel" to the cover movement, thereby guiding the user to the extreme limits of cover movement, where the spring 28 engages one of the abrupt walls 34.

Figure 12:
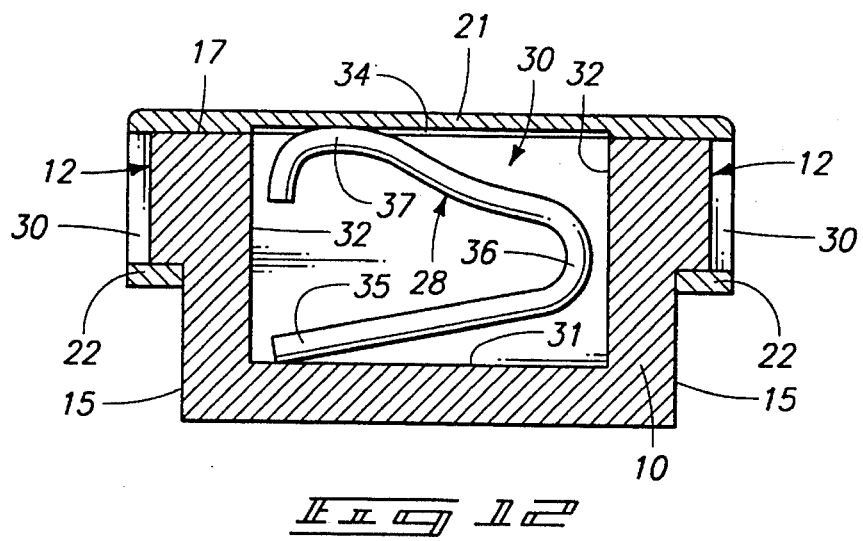
FIG. 12 is a sectional view taken along line 12—12 in FIG. 6, illustrating a first embodiment of a detent spring.

A first form of spring 28 is illustrated in FIG. 12. Spring 28 is shown as a flat spring having a first open end 35 in engagement with the recess base 31 at one side of the recess 30. The spring also includes an intermediate bent section 36 located toward the remaining side of the recess 30.

A bent end section 37 of the flat spring 28 overlies its open end 35. It serves as the bent spring section that is normally extended beyond the anterior surface 17 of the bracket across the fixed wall 24. The yieldable forces exerted on cover 21 by the engaged bent end section 37 maintains cover 21 in one or the other of its alternate conditions, as previously described.

Figure 13:
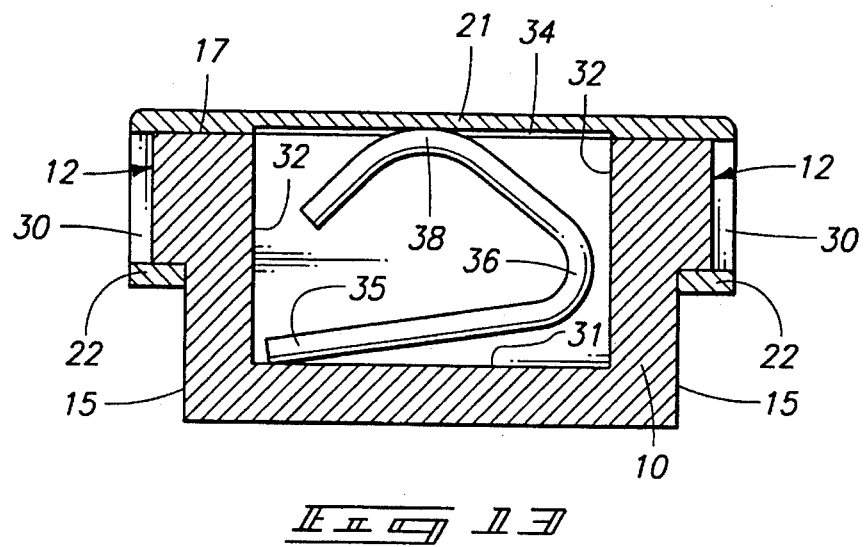
FIG. 13 is a view similar to FIG. 12, showing a second embodiment of the spring.
Figure 14:
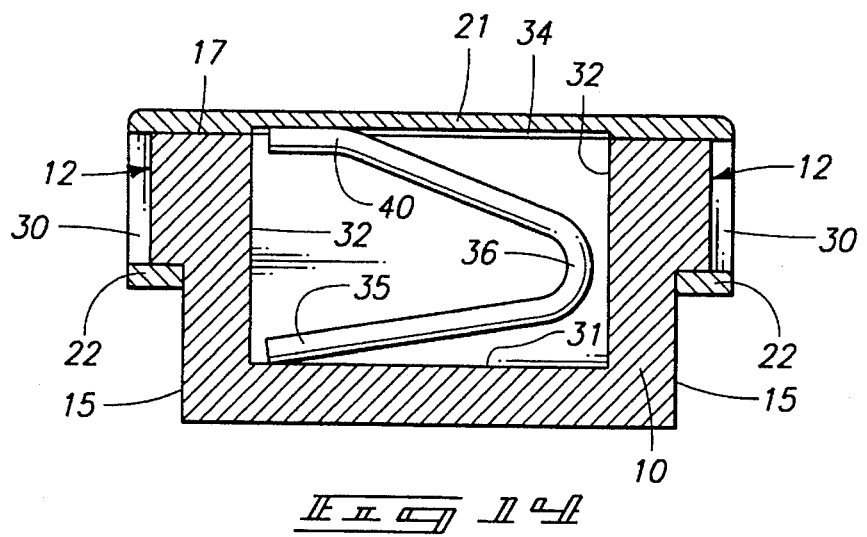
FIG. 14 is a view similar to FIG. 12, showing a third embodiment of the spring.

Two variations of the spring 28 configuration shown in FIG. 12 are illustrated in FIGS. 13 and 14, which use identical reference numbers to indicate common spring structure.

In FIG. 13, which is currently the preferred form, the spring 28 includes a bent end section 38 transversely centered within the bracket, the upper open end of spring 28 being bent downwardly upon itself. In FIG. 14, the bent end section 40 overlies the open end 35, at the one side of the recess 30, but terminates in a straight section that yieldably engages the inner surface areas of cover 21.

Figure 15:
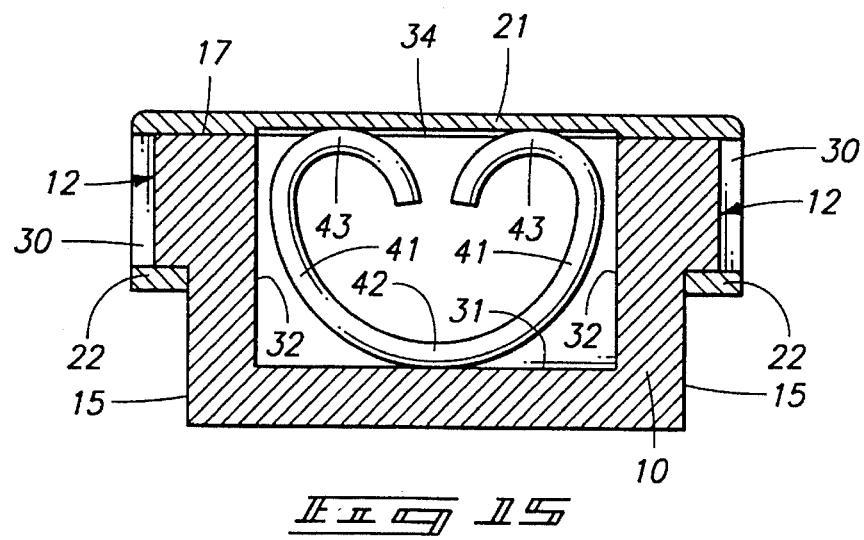
FIG. 15 is a view similar to FIG. 12, showing a fourth embodiment of the spring.
Figure 16:
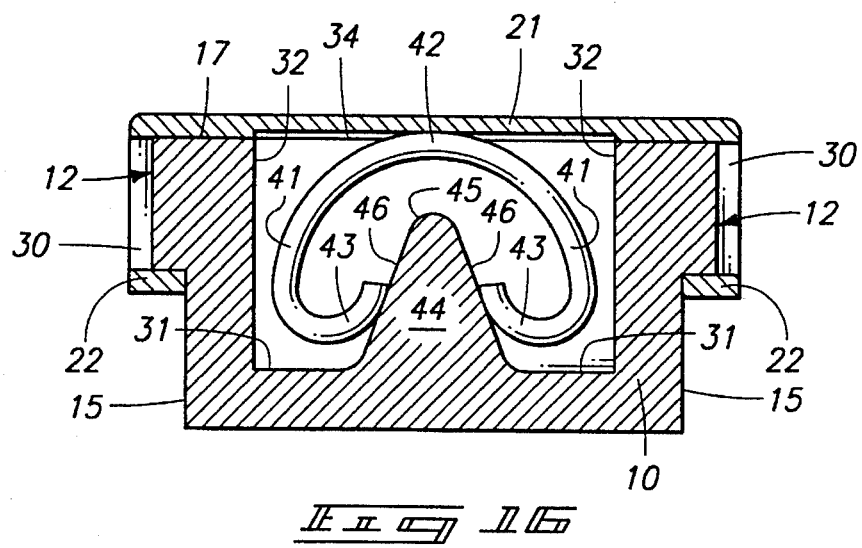
FIG. 16 is a view similar to FIG. 12, showing a fifth embodiment of the spring.
Figure 17:
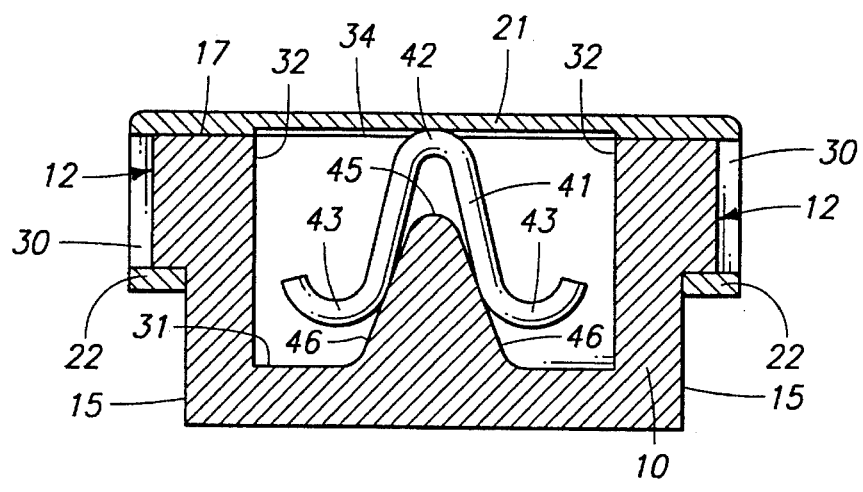
FIG. 17 is a view similar to FIG. 12, showing a sixth embodiment of the spring.
Figure 23:
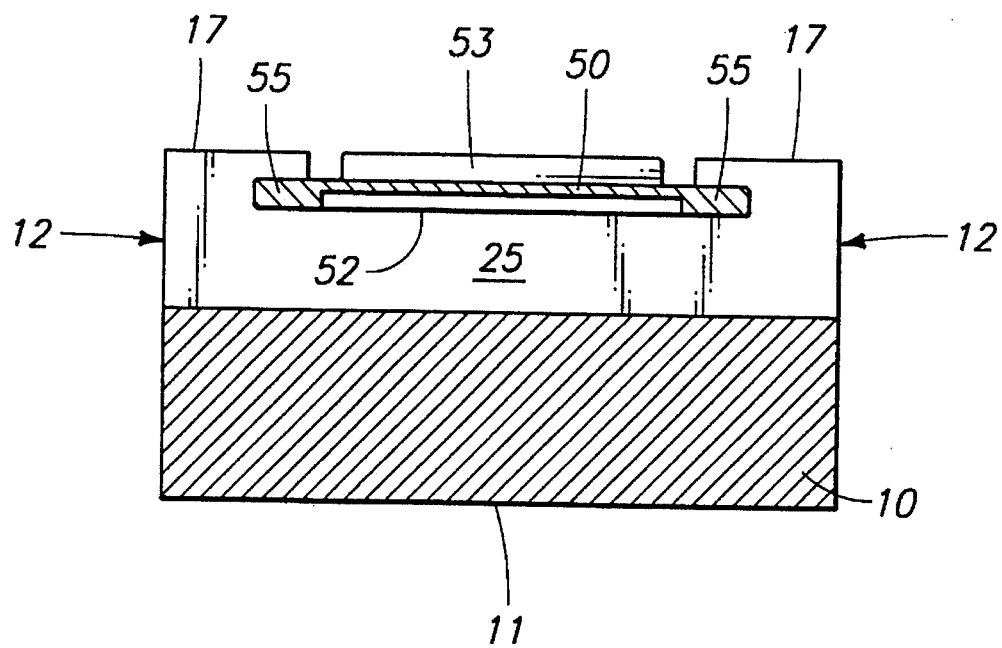
FIG. 23 is a sectional view taken along line 23—23 in FIG. 19.
Figure 24:
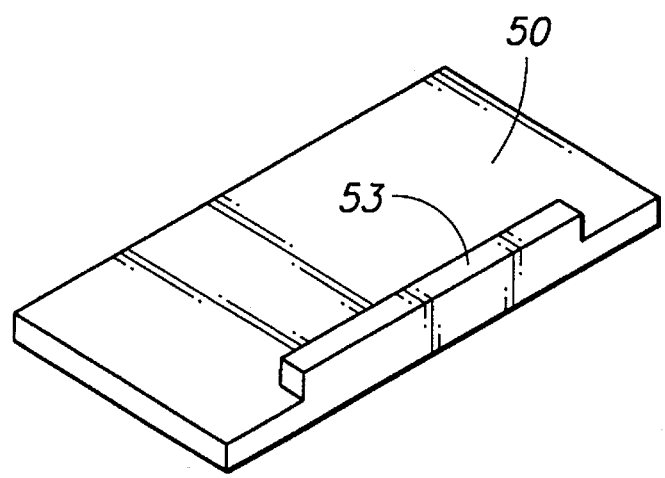
FIG. 24 is a top perspective view of the cover shown in FIGS. 18–23.
Figure 25:
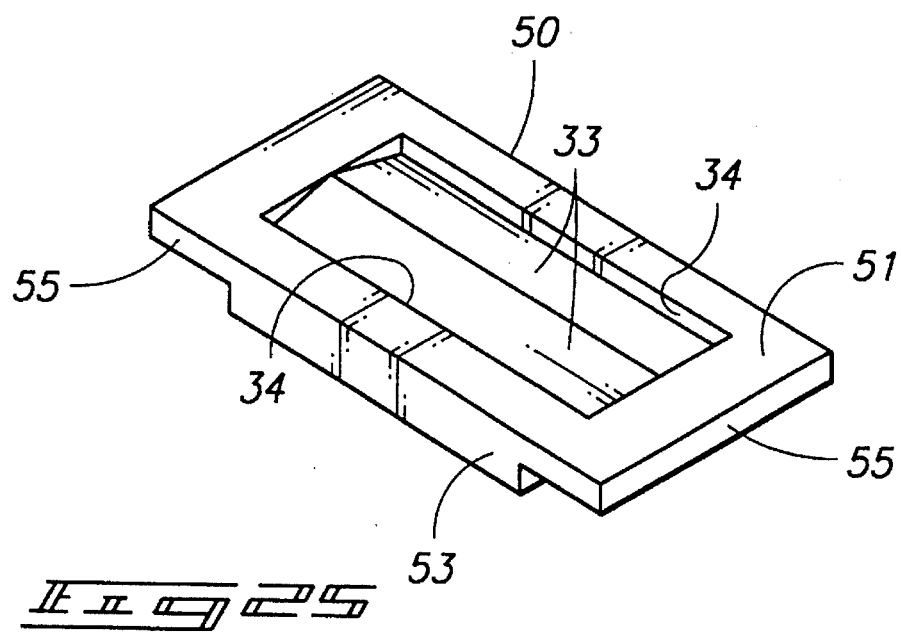
FIG. 25 is a bottom perspective view of the cover.

FIGS. 15, 16 and 17 illustrate springs 28 that have symmetrical curved sides 41, leading continuously from a curved central section 42. In FIG. 15, the curved central section 42 is in engagement with the recess base and the curved sides terminate in open ends 43 that normally extend beyond the anterior surface 17 of the bracket to engage the underside of cover 21.

In FIG. 16, a similarly-shaped spring is inverted and straddles a transversely centered divider 44 protruding anteriorly from the recess base 31 to an outer end 45 located inwardly within the recess with respect to the anterior surface 17 of the bracket. The divider 44 has side surfaces 46 that converge from the recess base 31 to its outer end 45. As shown in FIG. 16, the opened ends 43 of spring 28 are bent inwardly at a smaller radius than the radius of the curved sides 41 and slidably engage the side surfaces 46 of divider 44. The normal separation between the open ends 43 of spring 28 is such as to maintain the open ends 43 in engagement with the side surfaces 46 at an elevational position spaced from the recess base 31. Thus, the divider 44 facilitates flexing of spring 28 in response to forces imposed upon it by movement of cover 21.

FIG. 17 is similar to FIG. 16, but the open ends 43 are curved outwardly. The sides 41 of the spring, which are substantially straight, slidably engage the side surfaces 46 of divider 44.

All of the illustrated embodiments of spring 28 basically serve the same purpose—providing a protruding section of a flat spring that normally extends beyond the anterior surface 17 of the bracket to engage a complementary indentation formed across the posterior surface of cover 21. Whether the spring engages the cover at one side (FIGS. 12, 14, at its center, FIGS. 13, 16 and 17) or at both sides (FIG. 15) is a matter of design choice.

It is to be understood that the configuration of the indentation can be varied substantially from that shown specifically in the referenced drawings. For example, when using a spring 28 that engages the indentation at one side of cover 21, the indented area engaged by it can be confined to that side only. The indentation might also be shaped differently to provide greater or lesser retaining forces in one or the other of its positions. Such modifications are believed to be well within the design skill of those familiar with spring biased detents.

The sliding support provided to cover 21 in a direction parallel to the anterior surfaces of the bracket assures that forces applied to the bracket by the archwire will not result in accidental release of the cover from the bracket when installed in the mouth of a patient. Any outwardly directed forces exerted by the archwire will be resisted by the stiff structure of cover 21, guides 22, and support members 30. These elements should be constructed to withstand any foreseeable archwire forces without substantial deformation. In addition, flat spring 28 and the complementary indentations must be designed to hold cover 21 in a locked condition after installation in the mouth. The preferred transverse orientation of spring 28 permits it to provide substantial resistance to cover movement during normal usage of the bracket within the mouth of a patient. However, the cover remains readily releasable to specifically directed forces applied by professionals during installation and adjustment of the bracket and archwire.

It is also important to note that the resilient spring 28 only holds the cover 21 in an open or closed position. It is not utilized to hold the archwire in place within the archwire slot, nor does it hold the cover against the bracket itself. This is to be contrasted with earlier proposed covers for brackets, which have proposed pivoting the cover so that the holding arrangement for the cover must withstand forces exerted by the archwire if it is to remain in a closed position during use. This is true also with respect to previously proposed covers that clip over the bracket in opposition to the archwire extending across the bracket.

The bracket and closure can be mounted on a tooth in the conventional manner with the open edge of the closure facing toward the gingival line or the incisal or occlusal line.

Figure 26:
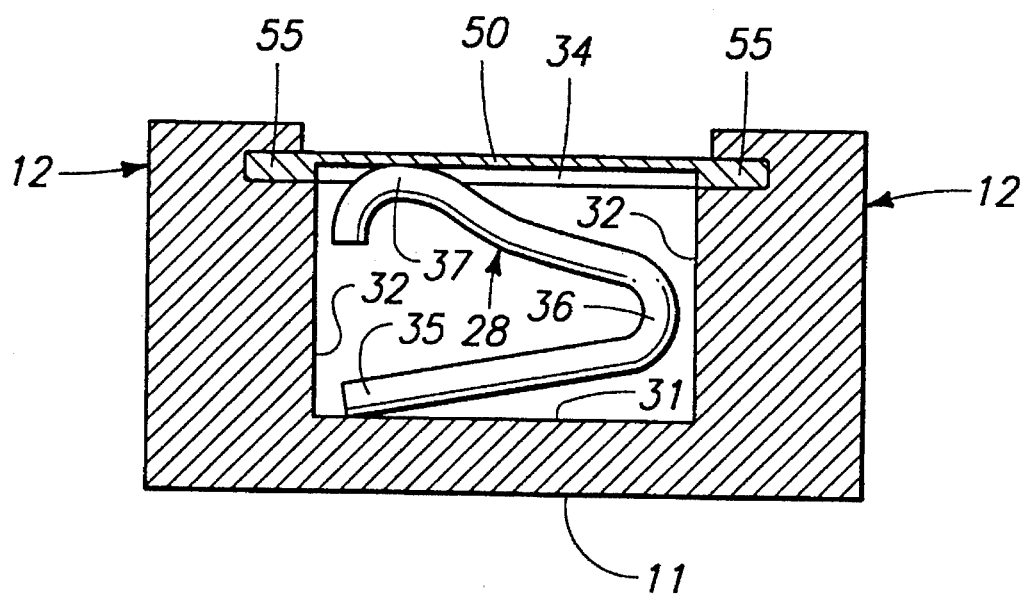
FIG. 26 is a sectional view taken along line 26—26 in FIG. 22.
Figure 27:
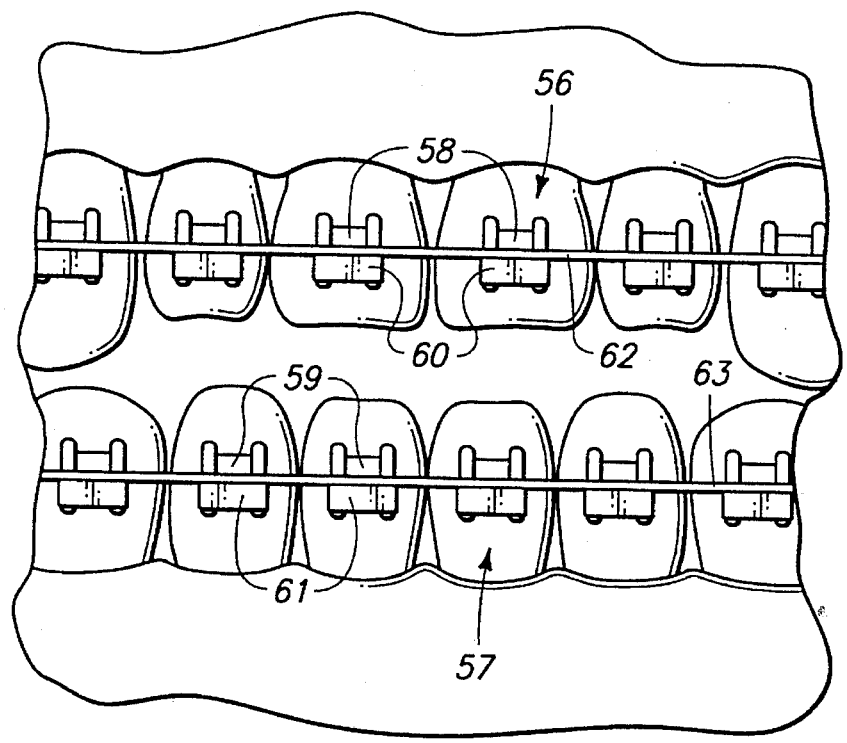
FIG. 27 is a fragmentary view illustrating use of the brackets on upper and lower teeth, showing the brackets in an open condition.

While it is not to limit the disclosure in any manner, a preferable mounting arrangement of the brackets is illustrated in FIGS. 26 and 27 and is detailed below.

FIGS. 18 through 26 illustrate a second embodiment of the invention. The reference numerals used in FIGS. 1 through 12 are applied to corresponding elements of the bracket shown in FIGS. 18–26, but the modified bracket is configured for use with an alternative cover 50.

Like cover 21 of FIGS. 1–12, the cover 50 in FIGS. 18–26 has a posterior surface 51 overlapping an anterior surface 52 across the bracket, but this anterior surface 52 is limited in width to the span separating the two lugs 12. The posterior surface of cover 50 slidably overlaps the anterior surface 52 of wall 24. Also, as previously described, the wall 24 can include a second spaced section 24', which is shown in dashed lines. While not necessary to the bracket structure, this second fixed wall section is desirable in order to extend the height of the anterior surface 52 and better visually reference the flush outer surface of an archwire (not shown) within the archwire slot that would be formed between the two sections.

Cover 50 is slidably received within inwardly facing grooves 54 formed across opposed side surfaces 16 of the bracket at locations anterior to the archwire slot. FIGS. 20–23 show that the opposed grooves 43 are located immediately adjacent to the anterior surfaces 52 across the fixed wall 24. They are recessed inwardly relative to the anterior surfaces 52 between the spaced lugs 12. The outer edges of cover 51 serve as guides 55 slidably received within the opposed grooves 54. As previously noted, the supporting grooves 54 preferably extend entirely across the bracket, but can be terminated at either side if desired.

Cover 51 is provided with an upturned lip 53 which simply serves as a handle to facilitate opening and closing of the cover. The remainder of the bracket, including the detent, is unchanged from the embodiment of FIGS. 1–17.

Figure 28:
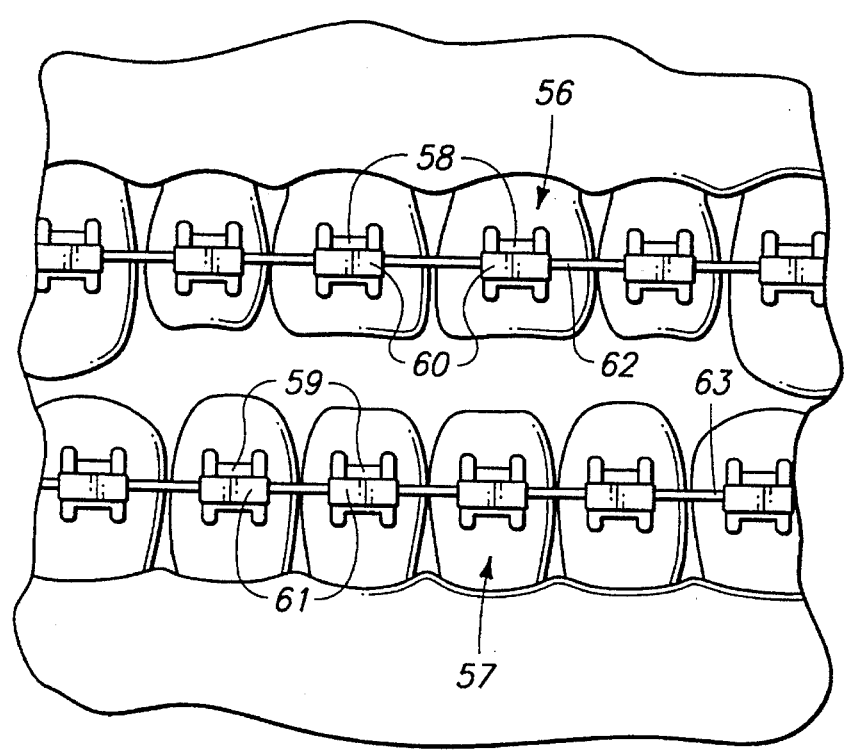
FIG. 28 is a view similar to FIG. 27, showing the brackets in a closed condition.

FIGS. 27 and 28 illustrate a preferred method for using the brackets of either embodiment. It is conventional to place self-locking brackets on teeth with the open edge of the closure facing toward the gingival line, as described in U.S. Pat. No. 5,275,557. When the above-described self-locking orthodontic brackets are arranged in two sets for attachment to the upper and lower teeth 56, 57 in conjunction with upper and lower archwires 62, 63, it is even more preferable to align the brackets so that the covers 60, 61 of both sets of brackets 58, 59 are movable to their respective first or second positions in a common direction relative to their supporting brackets.

It is to be noted that the set of brackets designed for attachment to the upper teeth 56 are constructed in the conventional manner, with covers 60 being superiorly or upwardly as they are closed. However, the set of brackets 59 for attachment to the lower teeth 57 are novel in that they also are moved to a closed position by moving them superiorly or upwardly. This is in stark contrast to the conventional design of brackets which are closed in a direction opposed to the biting forces across the gingival line.

As shown in the referenced drawing figures, the common direction of movement of the covers 60, 61 from their first or open position (FIG. 27) to their second or closed position (FIG. 28) is superior upward. To achieve this, the covers 60 in the upper set of brackets are opened toward the occlusal surfaces of the supporting upper teeth 56 by moving them superiorly or upwardly relative to the mouth of a patient. The covers 61 in the lower set are opened toward the incisal surfaces of the supporting lower teeth 57 by movement in the same direction as the covers 60 in the upper set of brackets. Conversely, the covers 60 in both sets of brackets are closed by selectively moving them inferiorly or downwardly relative to the mouth of a patient.

The orientation of the brackets and movable covers along each archwire facilitates visual referencing of the placement of the archwires within the brackets of both sets by attending professionals. The preferred orientation is with the covers closing upwardly and opening downwardly. Thus, when the covers are open, the attending professionals, who must view the archwires from above the mouth of a patient, can readily reference the archwire positions relative to the flush anterior surface areas 17 or 52 adjacent to the archwires 62 and 63.

The ability to design upper and lower sets of brackets covers movable in a common direction relative to the brackets stems from the fact that the described brackets utilize covers that are guided for movement independent of archwire forces that might be exerted upon them. As can be seen in the drawings, the forces exerted on the cover 21 by an archwire 62 or 63 will be in an anterior direction perpendicular to the supporting guides 22 along the cover structure. In addition, the locking forces exerted by the illustrated springs 28 are independent of cover movement. The only purpose of springs 28 is to hold the covers 21 in an open or closed condition—springs 28 do not retain the cover 21 in place on a supporting bracket nor do they act in opposition to archwire forces. Thus, the spring detents can be designed to positively lock the covers 21 on the supporting brackets and to resist forces that might be encountered within the mouth of a patient which tend to open the covers during normal eating and speech movements. The cover and detent designs described herein make it possible for the first time to focus upon the visualization needs of the attending professionals. By locating the open cover at the bottom of each bracket, shadows might otherwise be created by the cover structure across the archwire slot are eliminated and a clear view of the referencing anterior surfaces across the bracket is provided during archwire installation and adjustment.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A self-locking orthodontic bracket, comprising:

a bracket base having a posterior surface adapted to be bonded to a tooth;

a bracket projecting anteriorly from the bracket base;

the bracket including an anterior surface interrupted by an opening leading to an archwire slot;

a movable cover having a posterior surface overlapping the anterior surface of the bracket;

opposed guides on the cover that slidably support it on opposed side surfaces of the bracket for alternately positioning the cover in a first position clear of the archwire slot or a second position spanning the archwire slot;

the bracket having a recess open to its anterior surface;

a resilient flat spring mounted within the recess, the spring having a protruding section normally positioned beyond the anterior surface of the bracket;

the posterior surface of the cover including an indentation sized and positioned to receive the protruding section of the spring, the cover being releasably maintained in one of its first or second positions by engagement of the protruding section of the spring within the indentation.

2. The self-locking orthodontic bracket of claim 1, wherein the recess and flat spring are oriented transversely across the bracket.

3. The self-locking orthodontic bracket of claim 1, wherein the recess and spring are oriented transversely across the bracket, and the indentation is oriented transversely across the cover.

4. The self-locking orthodontic bracket of claim 1, further comprising:

a second indentation sized and positioned to receive the spring;

the cover being releasably maintained in the remaining one of its first or second positions by engagement of the protruding section of the spring within the second indentation.

5. The self-locking orthodontic bracket of claim 1, wherein the guides slidably engage opposed side surfaces of the bracket at locations posterior to the archwire slot.

6. The self-locking orthodontic bracket of claim 1, wherein the guides slidably engage opposed side surfaces of the bracket at locations anterior to the archwire slot.

7. The self-locking orthodontic bracket of claim 1, wherein the guides slidably engage opposed side surfaces of the bracket which face inwardly toward one another.

8. The self-locking orthodontic bracket of claim 1, wherein the guides slidably engaging opposed side surfaces of the bracket which face outwardly from one another.

9. The self-locking orthodontic bracket of claim 1, wherein the bracket includes outwardly projecting extensions.

10. A self-locking orthodontic bracket, comprising:

a bracket base having a posterior surface adapted to be bonded to a tooth;

a bracket projecting anteriorly from the bracket base, the bracket including transversely space side surfaces and an anterior surface interrupted by an opening leading to an archwire slot;

a movable cover having a posterior surface overlapping the anterior surface of the bracket;

opposed guides on the cover that slidably support it on opposed side surfaces of the bracket for alternately positioning the cover in a first position clear of the archwire slot or a second position spanning the archwire slot;

the bracket having a transverse recess open to its anterior surface and extending distally to a recess base between opposed recess end walls;

a resilient flat spring formed from a length of wire, the flat spring being movably mounted within the recess and including a protruding section that normally extends beyond the anterior surface of the bracket;

the posterior surface of the cover including at least one indentation sized and positioned to receive the protruding section of the spring, whereby the cover is releasably maintained in one of its first or second positions by engagement of the bent section of the spring within the indentation.

11. The self-locking orthodontic bracket of claim 10, wherein the flat spring has a first open end in engagement with the recess base at one side of the recess, an intermediate bent section located toward the remaining side of the recess, and a bent end section that overlies its first open end at the approximate center of the recess and is normally extended beyond the anterior surface of the bracket.

12. The self-locking orthodontic bracket of claim 10, wherein the flat spring has a first open end in engagement with the recess base at one side of the recess, an intermediate bent section located toward the remaining side of the recess, and a bent end section that overlies its first open end and is normally extended beyond the anterior surface of the bracket.

13. The self-locking orthodontic bracket of claim 10, wherein the flat spring has a first open end in engagement with the recess base at one side of the recess, an intermediate bent section located toward the remaining side of the recess, and a bent end section that overlies its first open end at the one side of the recess and is normally extended beyond the anterior surface of the bracket.

14. The self-locking orthodontic bracket of claim 10, wherein the flat spring has symmetrical curved sides leading continuously from a curved central section that normally extends beyond the anterior surface of the bracket, the curved sides terminating in open ends that are bent inwardly at a smaller radius than the radius of the curved sides.

15. The self-locking orthodontic bracket of claim 10, wherein the bracket further comprises:

a transversely centered divider protruding anteriorly from the recess base to an outer end located inwardly within the recess with respect to the anterior surface of the bracket, the divider having side surfaces that converge from the recess base to its outer end;

the flat spring having symmetrical curved sides leading continuously from a curved central section that normally extends beyond the anterior surface of the bracket, the curved sides terminating in open ends that are bent inwardly at a smaller radius than the radius of the curved sides and slidably engage the side surfaces of the divider.

16. The self-locking orthodontic bracket of claim 10, wherein the bracket further comprises:

a transversely centered divider protruding anteriorly from the recess base to an outer end located inwardly within the recess with respect to the anterior surface of the bracket, the divider having side surfaces that converge from the recess base to its outer end;

the flat spring having symmetrical sides leading continuously from a curved central section that normally extends beyond the anterior surface of the bracket, the curved sides terminating in open ends that are curved outwardly, and slidably engage the side surfaces of the divider.

17. The self-locking orthodontic bracket of claim 10, wherein the flat spring has symmetrical curved sides leading continuously from a curved central section in engagement with the recess base, the curved sides terminating in open ends that are bent inwardly at a smaller radius than the radius of the curved sides and that normally extend beyond the anterior surface of the bracket.

18. A self-locking orthodontic bracket, comprising:

a bracket base having a posterior surface adapted to be bonded to a tooth;

a pair of lugs projecting anteriorly from the bracket base in transversely spaced parallel positions;

the lugs including anterior surfaces interrupted by openings leading to an archwire slot formed distally from the anterior surfaces;

a fixed wall on the bracket base, the fixed wall being located between the lugs and along one side of the archwire slot, the fixed wall including an anterior surface;

a movable cover having a posterior surface overlapping the anterior surface of the fixed wall;

opposed guides on the cover and slidably supporting the cover on the pair of lugs for alternately positioning the cover in a first position clear of the archwire slot or a second position spanning the archwire slot;

the fixed wall having a recess at its anterior surface;

a resilient flat spring movably supported within the recess, the spring having a normal configuration that partially extends beyond the anterior surface of the fixed wall;

the posterior surface of the cover including at least one indentation sized and positioned to receive a section of the spring, whereby the cover is releasably maintained in one of its first or second positions by engagement of the spring within the indentation.

19. The self-locking orthodontic bracket of claim 18, wherein the recess and spring are oriented transversely across the fixed wall.

20. The self-locking orthodontic bracket of claim 18, wherein the recess and spring are oriented transversely across the fixed wall, and the indentation is oriented transversely across the cover.

21. The self-locking orthodontic bracket of claim 18, further comprising:

a second indentation sized and positioned to receive the spring, whereby the cover is releasably maintained in the remaining one of its first or second positions by engagement of the spring within the second indentation.

22. The self-locking orthodontic bracket of claim 18, further comprising:

a second fixed wall located between the lugs and along the remaining side of the archwire slot.

23. The self-locking orthodontic bracket of claim 18, wherein the lugs include side surfaces transversely spaced from one another;

the guides slidably engaging opposed side surfaces of the lugs at locations posterior to the archwire slot.

24. The self-locking orthodontic bracket of claim 18, wherein the lugs include side surfaces transversely spaced from one another;

the guides slidably engaging opposed side surfaces of the lugs at locations anterior to the archwire slot.

25. The self-locking orthodontic bracket of claim 18, wherein the lugs include side surfaces transversely spaced from one another;

the guides slidably engaging opposed side surfaces of the lugs which face inwardly toward one another.

26. The self-locking orthodontic bracket of claim 18, wherein the lugs include side surfaces transversely spaced from one another;

the guides slidably engaging opposed side surfaces of the lugs which face outwardly from one another.

27. The self-locking orthodontic bracket of claim 18, wherein the lugs include outwardly projecting extensions.

28. A self-locking orthodontic bracket, comprising:

a bracket base having a posterior surface adapted to be bonded to a tooth;

a pair of upright tying lugs projecting anteriorly from the bracket base in transversely spaced parallel positions, the tying lugs each including a pair of opposed side surfaces transversely spaced from one another and at least one outwardly projecting extension located between the side surfaces;

the tying lugs each including aligned anterior surfaces interrupted by a openings leading distally from the anterior surfaces to form a transverse archwire slot, the archwire slot having inner slot surfaces that open through the side surfaces of each tying lug;

a fixed wall on the bracket base and joining the two lugs, the fixed wall being located along one side of the archwire slot and including an anterior surface;

a movable cover slidably engaging and flush with the anterior surface of the fixed wall, the cover overlapping the full transverse width of the fixed wall;

a pair of guides operably supporting the cover and slidably engaging opposed side surfaces on the respective tying lugs for alternately positioning the cover in (1) a first position with the cover clear of the archwire slot or (2) a second position with the cover overlapping the width and height of the archwire slot; and the movable cover having a posterior surface overlapping the anterior surface of the fixed wall;

the fixed wall having a recess open to its anterior surface;

a resilient flat spring mounted within the recess, the spring having a normal configuration that partially extends beyond the anterior surface of the fixed wall;

the posterior surface of the cover including at least one indentation sized and positioned to receive a section of the spring, whereby the cover is releasably maintained in one of its first or second positions by engagement of the spring within the indentation.

29. The self-locking orthodontic bracket of claim 28, wherein the guides slidably engage transverse surfaces formed along opposing side surfaces on the respective tying lugs.

30. The self-locking orthodontic bracket of claim 28, wherein the guides slidably engage transverse surfaces formed at locations posterior to the archwire slot along opposing side surfaces on the respective tying lugs.

31. The self-locking orthodontic bracket of claim 28, wherein the guides slidably engage transverse surfaces formed at locations posterior to the archwire slot along opposing side surfaces that face outwardly on the respective tying lugs.

32. The self-locking orthodontic bracket of claim 28, wherein the guides slidably engage transverse surfaces formed at locations posterior to the archwire slot, the transverse surfaces being formed over the full height of the opposing side surfaces that face outwardly on the respective tying lugs.

33. The self-locking orthodontic bracket of claim 28, wherein the guides are slidably received within open slots formed at locations anterior to the archwire slot along opposing side surfaces on the respective tying lugs.

34. The self-locking orthodontic bracket of claim 28, wherein the guides are slidably received within open slots formed at locations anterior to the archwire slot, the open slots being formed over the full height of the opposing side surfaces that face inwardly on the respective tying lugs.

35. A self-locking orthodontic bracket, comprising:

a bracket base having a posterior surface adapted to be bonded to a tooth;

a pair of tying lugs projecting anteriorly from the bracket base in transversely spaced parallel positions, the tying lugs each including a pair of opposed side surfaces transversely spaced from one another and at least one outwardly projecting extension located between the side surfaces;

the tying lugs each including aligned anterior surfaces interrupted by a transverse archwire slot leading distally from the anterior surfaces, the archwire slot having inner slot surfaces that open through the side surfaces of each tying lug;

a fixed wall on the bracket base, the fixed wall being located between the lugs and along one side of the archwire slot, the fixed wall including an anterior surface;

a movable cover slidably engaging and flush with the anterior surfaces of the tying lugs, the cover overlapping the full transverse width of the pair of tying lugs and having a perpendicular height that is greater than the height of the archwire slot across the anterior surfaces of the tying lugs;

a pair of guides operably supporting the cover and slidably engaging opposed side surfaces on the respective tying lugs at locations posterior to the archwire slot for alternately positioning the cover in (1) a first position with the cover clear of the archwire slot or (2) a second position with the cover overlapping the width and height of the archwire slot;

a pair of support members structurally interconnecting the cover and the pair of guides, the pair of support members being respectively located adjacent the opposed side surfaces of the tying lugs engaged by the pair of guides, each support member leading posteriorly from the cover to one of the guides;

the movable cover having a posterior surface overlapping the anterior surface of the fixed wall;

the fixed wall having a recess open to its anterior surface;

a resilient flat spring mounted within the recess, the spring having a normal configuration that partially extends beyond the anterior surface of the fixed wall; and the posterior surface of the cover including at least one indentation sized and positioned to receive a section of the spring, whereby the cover is releasably maintained in one of its first or second positions by engagement of the spring within the indentation.

36. The self-locking orthodontic bracket of claim 35, wherein the anterior surface of the fixed wall forms a continuous extension of the anterior surfaces of the tying lugs.

37. The self-locking orthodontic bracket of claim 35, wherein the anterior surface of the fixed wall forms a continuous extension of the anterior surfaces of the tying lugs and wherein the fixed wall further includes at least one transverse surface that forms a continuous extension of an inner slot surface that opens through the side surfaces of the tying lugs.

38. The self-locking orthodontic bracket of claim 35, wherein the anterior surface of the fixed wall forms a continuous extension of the anterior surfaces of the tying lugs and wherein the fixed wall further includes a pair of spaced transverse surfaces that form continuous extensions of the inner slot surface that open through the side surfaces of the tying lugs.

39. The self-locking orthodontic bracket of claim 35, wherein the guides slidably engage opposed side surfaces of the tying lugs at locations posterior to the archwire slot.

40. The self-locking orthodontic bracket of claim 35, wherein the guides slidably engage opposed side surfaces of the lugs which face outwardly from one another.

* * * * *